United States Patent
Martikka et al.

(10) Patent No.: US 9,993,162 B2
(45) Date of Patent: Jun. 12, 2018

(54) METHOD AND APPARATUS FOR CALCULATING PHYSIOLOGICAL TRAINING PARAMETERS

(75) Inventors: Mikko Martikka, Vantaa (FI); Erik Lindman, Espoo (FI)

(73) Assignee: AMER SPORTS DIGITAL SERVICES OY, Vantaa (FI)

( * ) Notice: Subject to any disclaimer, the term of this patent is extended or adjusted under 35 U.S.C. 154(b) by 680 days.

(21) Appl. No.: 13/071,624

(22) Filed: Mar. 25, 2011

(65) Prior Publication Data

US 2011/0263993 A1    Oct. 27, 2011

Related U.S. Application Data

(60) Provisional application No. 61/319,272, filed on Mar. 31, 2010.

(30) Foreign Application Priority Data

Mar. 26, 2010 (FI) ..................................... 20105310

(51) Int. Cl.
*A61B 5/02* (2006.01)
*A61B 5/0205* (2006.01)
(Continued)

(52) U.S. Cl.
CPC ............ *A61B 5/0205* (2013.01); *A61B 5/024* (2013.01); *A61B 5/4866* (2013.01);
(Continued)

(58) Field of Classification Search
CPC ....... A61B 5/024; A61B 5/021; A61B 5/0002; A61B 5/02438
(Continued)

(56) References Cited

U.S. PATENT DOCUMENTS 6,537,227 B2    3/2003  Kinnunen et al.
7,043,294 B1 *  5/2006  Paris ............................. 600/519
(Continued)

FOREIGN PATENT DOCUMENTS

EP    1 147 790 A2    10/2001
EP    2 095 763 A1    9/2009
(Continued)

OTHER PUBLICATIONS

Cole et al., Heart-rate Recovery Immediately After Exercise as a predictor of Mortality, NJM, vol. 341(18), pp. 1351-1357, Oct 1999.*
(Continued)

*Primary Examiner* — Tiffany Weston
*Assistant Examiner* — Tho Tran
(74) *Attorney, Agent, or Firm* — Birch, Stewart, Kolasch & Birch, LLP

(57) ABSTRACT

The present invention relates to a method and apparatus for determining an exercise parameter during a physical performance or after it. In the method the pulse of the heart is measured by means of a sensor, the pulse value is determined on the basis of the measurement and the said exercise parameter is calculated on the basis of the pulse value. According to the invention, a recovery pulse value is determined on the basis of the pulse value and previously determined pre-data, the value being dynamically varied during the exercise and the said exercise parameter being defined by using the recovery pulse value. With the invention, it is possible to accurately estimate the recovery time required after the performance as well as the energy consumption during the performance.

20 Claims, 10 Drawing Sheets

(51) Int. Cl.
    *A61B 5/024*     (2006.01)
    *A61B 5/00*      (2006.01)
    *A63B 24/00*     (2006.01)
    *G06F 19/00*     (2018.01)
(52) U.S. Cl.
    CPC ...... *A63B 24/0062* (2013.01); *G06F 19/3481* (2013.01); *A63B 2024/0065* (2013.01); *A63B 2230/04* (2013.01); *A63B 2230/75* (2013.01)
(58) Field of Classification Search
    USPC .................................................. 600/500–503
    See application file for complete search history.

(56)         References Cited

U.S. PATENT DOCUMENTS 7,192,401 B2    3/2007   Saalasti et al.
    7,460,901 B2   12/2008   Kettunen et al.
    2002/0188178 A1*  12/2002  Toeppen-Sprigg ........... 600/300
    2006/0004265 A1    1/2006  Pulkkinen et al.
    2007/0027399 A1*   2/2007  Chou ........................... 600/523
    2007/0249949 A1   10/2007  Hadley

FOREIGN PATENT DOCUMENTS

WO    WO 2007/099206 A1    9/2007
    WO    WO 2009/118645 A1   10/2009

OTHER PUBLICATIONS

Myers et al. "Effects of exercise training on heart rate recovery in patients with chronic heart failure." American Heart Journal Online, Feb. 2, 2007, pp. 1056-1062.
Miriam Lacasse et al., "Post-exercise heart rate recovery and mortality in chronic obstructive pulmonary disease" Respiratory Medicine(2005) 99, pp. 877-886.

* cited by examiner

METHOD AND APPARATUS FOR CALCULATING PHYSIOLOGICAL TRAINING PARAMETERS

CROSS REFERENCE TO RELATED APPLICATIONS

This nonprovisional application claims the benefit of U.S. Provisional Application No. 61/319,272 filed on Mar. 31, 2010 and to Patent Application No. 20105310 filed in Finland on Mar. 26, 2010. The entire contents of all of the above applications is hereby incorporated by reference.

BACKGROUND OF THE INVENTION

Field of the Invention

The present invention relates to a method of calculating exercise parameters during or after training performance. The invention especially relates to a method based on pulse measurement for estimating the necessary recovery time after an exercise and the energy consumption related to the exercise. The invention also relates to a corresponding apparatus.

Description of Background Art

There are a number of prior art methods for estimating recovery time and energy consumption on the basis of pulse measurement. Such methods are disclosed in. e.g. publications EP 1147790, U.S. Pat. No. 7,192,401, U.S. Pat. No. 7,460,901, US 2006/0004265, WO 2007/99206 and WO 2009/118645.

For example, in the method disclosed in publication U.S. Pat. No. 7,192,401 the recovery time is estimated on the basis of pulse measurement using a weight value table depending on the intensity of the exercise and independent of the duration of the exercise.

In the method disclosed in publication WO 2009/118645 the recovery time is estimated using a metabolic and mechanical component. The metabolic component is estimated on the basis of the physical exertion of the exercise, for which the protein combustion speed related to the exercise is estimated.

Pulse measurement, more exactly the periodicity of the pulse intervals, has also been used for estimating the breath frequency of a person and that way for more accurately estimating the energy consumption and recovery time. One such method has been described e.g. in publication U.S. Pat. No. 7,460,901. The disadvantage of these methods is, however, the mathematical complexity and the fact that the measured pulse data must be of a very high quality in order to be at all able to determine breath frequency on the basis of the periodicity of the pulse interval noise. The inaccuracy of the pulse interval measurement is caused by the movement of the measurement sensors and the breakages of data transfer, among others. Thus, in practice there is inaccuracy in the calculation of the breath frequency. Further, the response time of a human heart to a change is measured in seconds.

This problem can be eliminated by going directly into pulse or mean pulse based methods, but then the "physiological" calculation accuracy created by the knowing of the breath frequency is lost. Mean pulse is. however, much easier to determine during an exercise than breath frequency.

One problem with both the known energy consumption calculations as well as the known recovery time calculations is that even though the methods would work well in one sports, they can give very incorrect values in another sports.

It can be said as a conclusion that even though a lot has been invested in pulse-based calculation of energy consumption in recent years, the known methods are still considerably lacking.

SUMMARY AND OBJECTS OF THE INVENTION

The purpose of the invention is to reduce the above-mentioned problems and to provide a method by means of which the nature of the exercise, i.e. the load of the exercise and further the physiological effect of it, is taken better into account.

The purpose of the invention is especially to provide a method feasible based on mean pulse, and thus having an easier measurement technique and being generally more reliable for calculating the exercise parameters.

The invention is based on the idea that the exercise parameter is calculated by a data processing unit 1 including a pulse sensor 2 as shown in FIG. 6, by using recovery pulse, i.e. an estimated pulse level dynamically updated during the exercise and to which the pulse of the person recovers in a certain time when the exercise is ended. In more detail, in the method, the pulse of the heart is measured by means of the pulse sensor 2,
a pulse value is determined by the data processing unit 1 on the basis of the measurement,
recovery pulse value is determined on the basis of the current pulse value and predefined pre-data, the recovery pulse value being dynamically variable during the exercise,
said exercise parameter is determined by the data processing unit 1 by using the recovery pulse value.

The dynamic variation of recovery pulse value means that the value is updated on the basis of the pulse data collected from the exercise during the exercise. Preferably, updating is done recursively by using the previous recovery pulse value and the current pulse value. According to one embodiment at least one pre-data, such as the saturation level of the pulse and/or the change speed of the saturation level of the pulse, tabulated in relation to the current pulse, is used in addition to these data.

The pulse value can be the real pulse frequency. According to an advantageous embodiment a pulse value derived from the real pulse frequency HR is used as the pulse value taking into account the effect of the resting pulse of the person. Such a pulse level is arrived at by a formula in which the factor is the subtraction of the real pulse frequency HR and the resting pulse HRrest (HR−HRrest). Especially preferably the real pulse is put into relation with the pulse range the athlete theoretically has available during the exercise, i.e. to the "pulse reserve". Such a pulse value is arrived at by using a formula in which the factor is (HR−HRrest)/(HRmax−HRrest), in which HR is the real pulse, HRrest is the resting pulse of the person and HRmax is the maximum pulse of the person.

The recovery pulse value is determined on the basis of the current pulse value and the pre-data. Most usually, the pre-data are tabulated or modeled data about the saturation level of the recovery pulse which is the result of the current exercise intensity in case the exercise is continued long enough. Usually this information is dependent on the sports. Pre-data also preferably includes information about the current fitness level of the person, i.e. an index describing the fitness level of the person.

According to one embodiment the recovery pulse value is determined recursively by using a previously defined recovery pulse value, whereby in the method a first table, attaching pulse values with saturation levels of recovery pulse level corresponding therewith, is used, the saturation level of the recovery pulse value corresponding with the current pulse level being then read from the table and the recovery pulse value being changed on the basis of the said saturation level.

In case the recovery pulse value is defined for the first time using this algorithm, a predefined initial recovery pulse level, such as resting pulse, can be used as the previously determined recovery pulse value.

According to one embodiment, the contents of the first table are chosen on the basis of whether the current pulse value is larger or smaller than the previously defined recovery pulse value.

According to a preferred embodiment the recovery pulse value is increased always if the saturation level is larger than the previously defined recovery pulse value and reduced if the saturation level is smaller than this. The difference between the saturation level and the previously defined recovery pulse defines at least partly the amount of the necessary change.

According to one embodiment, a second table is additionally used for determining the recovery pulse level, the table attaching pulse values with saturation speed factors corresponding therewith, a saturation speed factor corresponding to the current pulse level being read from the second table and the recovery pulse value being changed on the basis of the said saturation level and the saturation speed factor.

Preferably the content of the second table is chosen on the basis of an index describing the fitness of the person. This is done because the recovery pulse of a fit person changes slower than a person less fit, i.e. after a certain exercise time the pulse of a fit person recovers faster to a lower level than that of a less fit person.

Further, the main purpose of the invention, calculation of an exercise parameter, is most preferably carried out by deducting the recovery pulse value defined from the current pulse value for producing a changed pulse value and by further calculating the said exercise parameter by using the changed pulse value. In other words, the physiological effect of the exercise is modeled at each point in time in addition to current pulse level, also on the basis of the recovery pulse level changing during the exercise.

According to one embodiment the exercise parameter calculated on the basis of the recovery pulse cycle is the recovery time describing the rest time needed for fully recovering from the current exercise.

The recovery time can be recursively calculated on the basis of an earlier defined recovery time so that each time when the current pulse level exceeds the defined recovery pulse level, the recovery time is increased, and each time when the current pulse level is lower than or equal to the defined recovery pulse value, the recovery time is reduced.

In the beginning of the exercise the recovery time can be zero or, alternatively, a non-zero initial value, if recovery from the previous exercise is not complete yet.

Further, the recovery time is calculated on the basis of the so-called effective exercise time, the effective exercise time being calculated from the actual pulse frequency and the maximum performance pulse, the maximum performance pulse preferably being chosen depending on the type of the discipline of the athlete.

Preferably the recovery time is calculated by also taking into account an index describing the fitness level of the person as the fitness level has an effect on the ability of the body to recover from an exceptional condition caused by physical exertion.

According to one embodiment the exercise parameter calculated on the basis of the recovery pulse value is energy consumption.

The energy consumption can be calculated by converting the pulse value into oxygen consumption value and the energy consumption is calculated on the basis of the oxygen consumption value with a function dependent on the sex, age and index describing the fitness level of the person. Most preferably the pulse value is converted into oxygen consumption value with a different conversion depending on whether the pulse value is smaller or larger than the recovery pulse, whereby it is possible to take into account the observed effect of changes in the intensity of the exercise to the energy consumption.

Considerable advantages are achieved by means of the invention. In particular, the invention can be used for estimating the physiological effects of the exercise, especially energy consumption and recovery time, very accurately without pulse interval measurement. This is due to the fact that according to the invention the recovery pulse that can be estimated on the basis of the measured pulse and suitable pre-data, as is described in more detail hereinafter, gives an accurate figure of the exertion of the exercise. Because the pulse frequency measurement is a considerably more reliable measurement than pulse interval measurement, the invention eliminates a problem with the lack of reliability relating to the measurement error of known solutions. One advantage of the present recovery calculation is that recovery time is connected to real observations about recovery requirements—not to hypotheses about how a disturbance of metabolics is recovered on the basis of a model, as in some prior art methods.

The basic principle of the invention and some most important embodiments are generally described above. Other embodiments and advantages and closer details and mathematical formulae for carrying put the invention in practice in at least one way are shown in the following detailed description with reference to the appended drawings.

DEFINITIONS

Figure 1A:
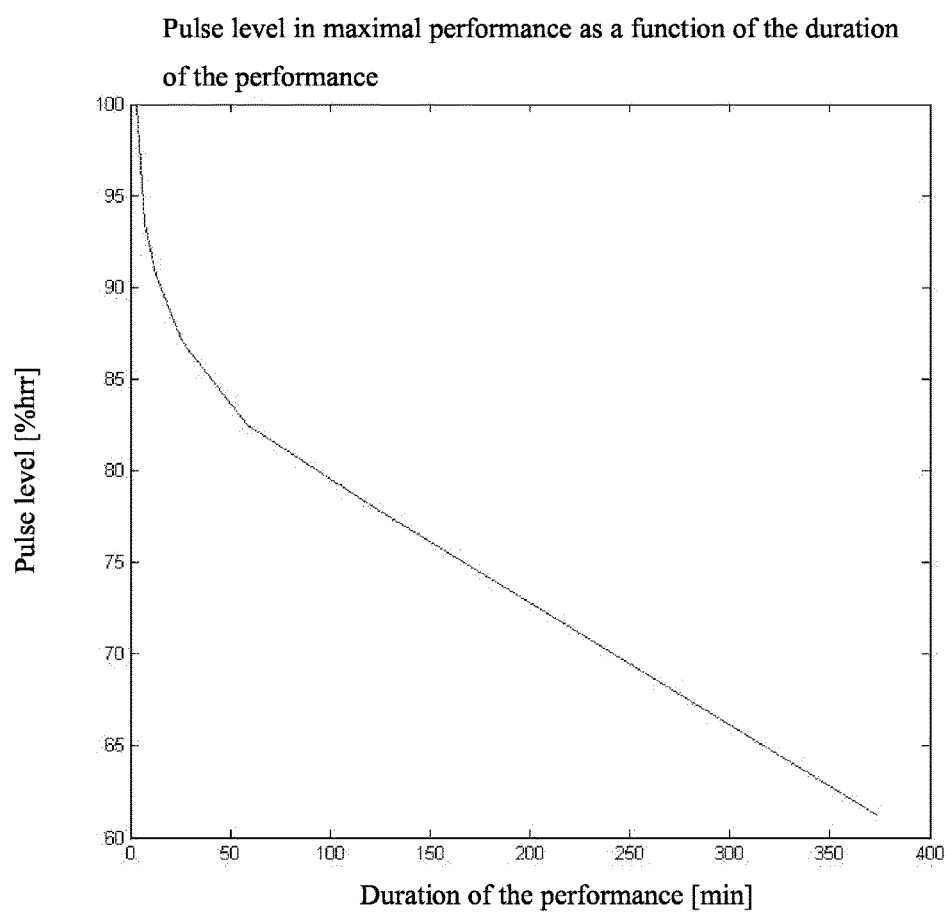
FIG. 1a shows the pulse of a human in a maximum performance exercise as a percentage of maximum pulse.

Hereinafter the abbreviation HR is used to refer to the absolute pulse frequency and the abbreviation hrr is used to refer to the relation of the difference between the pulse frequency and the resting pulse to the pulse reserve (the unit being typically "percentage of the pulse reserve"). Unless stated otherwise or it can be otherwise understood, the terms "pulse value" and "pulse level" cover both of the above-mentioned concepts and other derivatives also describing the intensity of the exercise formed on the basis of the pulse measurement using some conversions.

More specific definitions and their derivatives are described below.

"Recovery pulse" ($HR_{recovery}$/$hrr_{recovery}$) means a pulse level achieved when the exercise is interrupted and the person stays still. In reality the recovery pulse can be measured as mean pulse over a certain time after the interruption of the exercise or after a certain period of time subsequent to the interruption. During an arbitrary exercise the recovery pulse depends on the performed work and the duration of the exercise. In the present method the recovery pulse is dynamically estimated by means of calculation as the exercise progresses without the need for interrupting the exercise. In other words, each point of time of the exercise corresponds to a recovery pulse reading that could (in an ideal case) be measured if the exercise were interrupted and the person stayed still.

In both main applications of the invention—recovery time calculation and energy consumption calculation—the recovery pulse is utilized. An exemplary method of defining recovery pulse is described hereinafter.

"The saturation level of recovery pulse" ($HR_{sl}$/$hrr_{sl}$) is a level to which the recovery pulse increases when the current intensity is carried on for sufficiently long. The saturation level depends on, in addition to the intensity of the exercise, also on the fitness level of the person. The saturation levels for various pulse levels can be modeled and tabulated. In practice the level can be estimated from the pulse measurements of maximal and submaximal tests. Interval-type exercises can also provide good estimates for the saturation levels of the recovery pulse. Typically the saturation level of the recovery pulse is from 0 to 50 percent, especially from 0 to 30 percent of the pulse reserve, depending on the intensity of the exercise on an intensity scale of 0 to 100 percent of the pulse reserve.

The "saturation coefficient of recovery pulse" ($sl_{coeff}$), on the other hand, is a change speed relating to the saturation level by means of which the said saturation level is achieved. Also the saturation level depends on, in addition to the intensity of the exercise, on the fitness level of the person as well. The saturation level can as well be modeled for example so that its values are chosen so that the average error of the final quantity (such as energy consumption) is minimized in relation to a reference measurement. Further, the modeled saturation coefficients can be tabulated. Typically the saturation level varies from 0 to 0.15, especially from 0 to 0.10 depending on the intensity of the exercise, on an intensity scale of 0 to 100 percent of the pulse reserve.

Figure 1B:
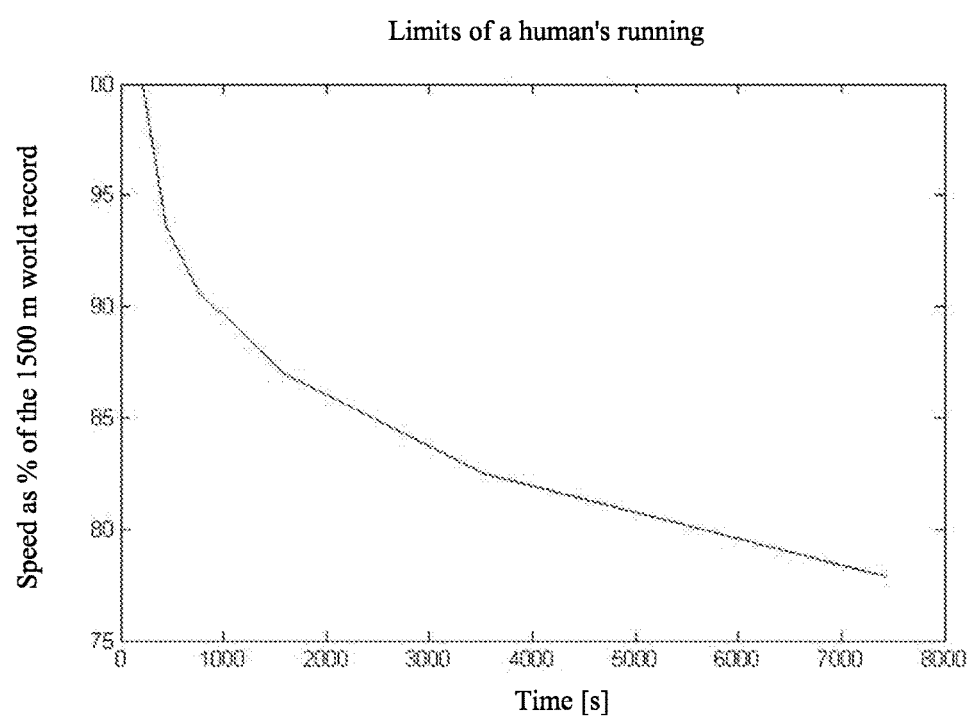
FIGS. 1b and 1c show the limits of a human's running as a percentage of maximum speed in relation to the world records of 1500 m and 100 m, respectively.
Figure 1C:
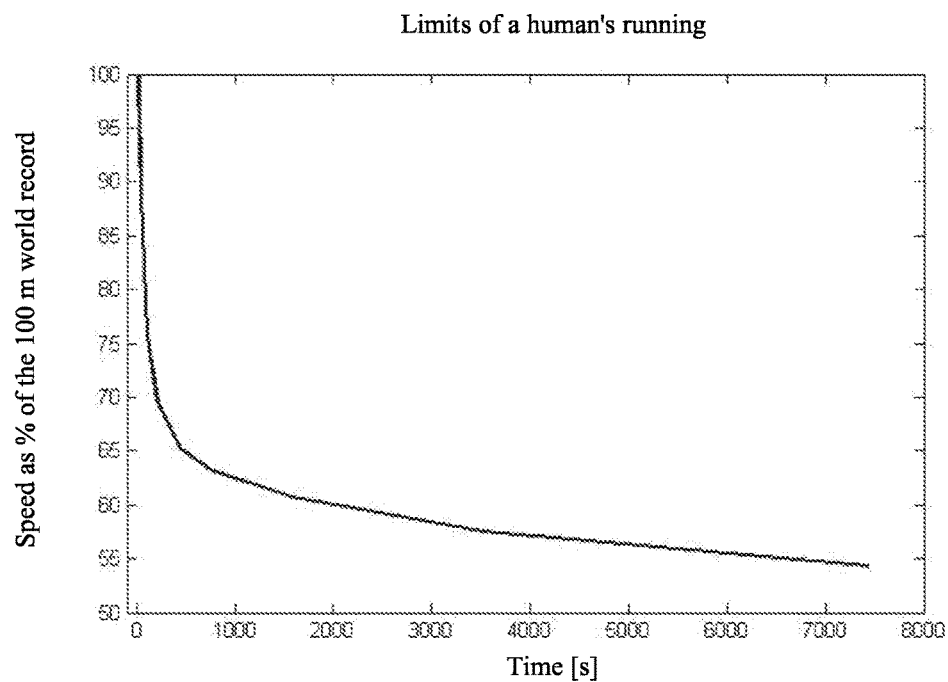

The "maximum performance pulse" ($HR_{maxperf}$/$hrr_{maxperf}$) means the highest pulse level a person can maintain to achieve a certain time/distance goal. The maximum performance pulse changes (decreases) as the exercise progresses and it is always smaller than the maximum pulse corresponding to the highest possible heartbeat rate of a person. In practice the maximum performance pulse is discipline-specific and differently standardized maximum pulse tables or functions can be made for different disciplines. FIG. 1a shows an example of a human's maximum performance pulse as a percentage of maximum pulse in a maximum performance as a function of running time (up to about 6 hours). The curve has been made by using the world records current in running disciplines at the beginning of 2010 (iaaf.org). FIGS. 1b and 1c show the theoretical limits of a human's running speed in relation to the world records of 1500 m and 100 m, respectively. The curve of FIG. 1a has been formed by assuming the 1500 m record corresponds to a maximal aerobic speed and the maximum pulse of a person. The curve must be interpreted so that if a person plans to run a maximum performance with a duration of three hours, the average pulse of the performance must be at the most about 75% of the pulse reserve. This, of course, requires that the athlete has exercised endurance properties sufficiently and is in top condition. Similar curves can be correspondingly formed for other disciplines than running events as well.

"Pulse reserve" means the pulse range between a person's resting pulse ($HR_{rest}$) and maximum pulse ($HR_{max}$), where the pulse (HR) practically always is.

Figure 2:
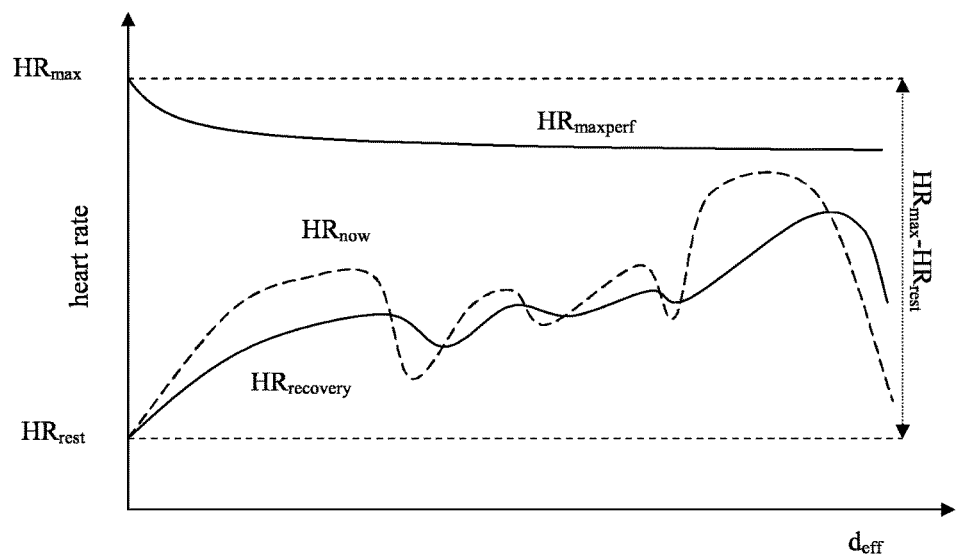
FIG. 2 shows schematically the absolute resting and maximum pulse limits and the maximum performance pulse and recovery pulse changing in relation to the performance.

FIG. 2 illustrates the above-mentioned concepts graphically using an example performance.

DETAILED DESCRIPTION OF THE PREFERRED EMBODIMENTS

The current pulse is described by the term $HR_{now}$/$hrr_{now}$.

The terms "old" and "new" refer to a previous and a new value, correspondingly, in recursive calculation. The term "now" refers to the current measured pulse value.

Effective exercise time ($d_{eff}$) refers to exercise time taking the exertion level of the exercise into account. Thus the effective exercise time corresponding to a light performance is smaller than the effective exercise time of the same duration but with a heavier exertion.

The "fitness index" means a quantity describing the general condition of a person and it can be entered by the user or it can be automatically determined. Here, the fitness index especially means classification on Shvarz and Reibold scale 1 to 7 and derivatives thereof. For example, the scale 1 to 7 can be continued by extrapolating the modified functions for producing a fitness index on the range of 0 to 10 extended to outside the observation range. This extended index can be made so that it can be arranged to the Shvarz and Reibold material on the range 1 to 7 and when the age of the exercising person is 10 to 70 years.

Oxygen consumption reserve means the difference between the maximum oxygen consumption and resting consumption of a person.

Estimating the Recovery Pulse

According to one embodiment the recovery pulse is recursively estimated on the basis of current pulse by using the resting pulse and the maximum pulse of a person as pre-data. These parameters can be typically entered into the apparatus by the user or the apparatus can define them automatically by means of a software application. In the present calculation the resting pulse can be constant regardless of the person, e.g. 60 bpm, which is a good average estimate. The method proceeds by steps as follows:

1. The pulse (HR) is measured and it is converted into a percentage of the pulse reserve:

$$hrr_{now} = (HR - HR_{rest}) * 100\% / (HR_{max} - HR_{rest})$$

2. The saturation level ($hrr_{sl}$) of the current pulse level ($hrr_{now}$) is read from a table, the saturation level being also the pulse reserve percentage in unit.

3. The current recovery pulse level ($hrr_{recovery\_old}$) is updated towards the saturation level by means of a saturation coefficient ($sl_{coeff}$) read from the table for producing a new recovery pulse level ($hrr_{recovery\_new}$). The update equation can be e.g. of the form $$hrr_{recovery\_new} = hrr_{recovery\_old} + sl_{coeff} * (hrr_{sl} - hrr_{recovery\_old}).$$

4. If the current pulse level is lower than the saturation level read from the table, the contents of the tables for saturation level and saturation coefficient tables are chosen to correspond with the resting situation (off response). Otherwise the table values during exertion are used (on response).

Figure 7:
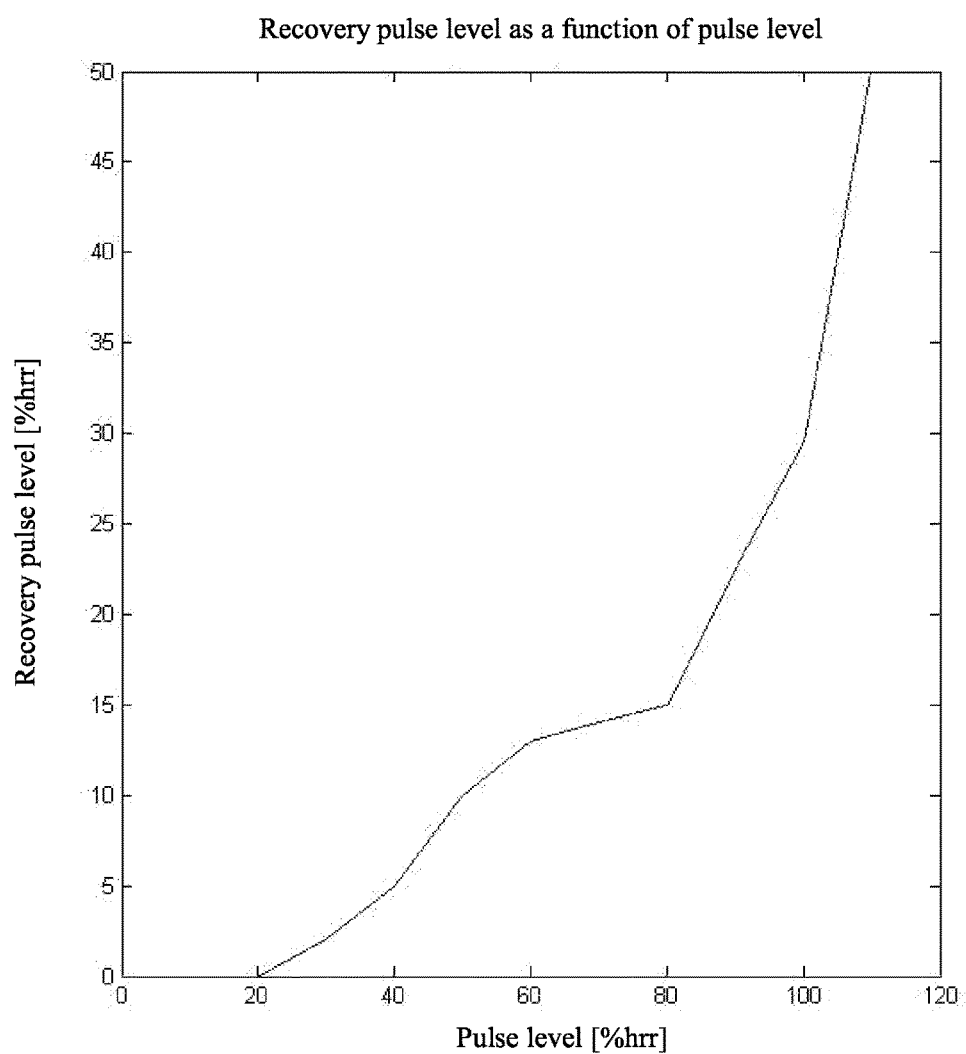
FIG. 7 shows an example of the saturation level function of recovery pulse on one fitness level.
Figure 8:
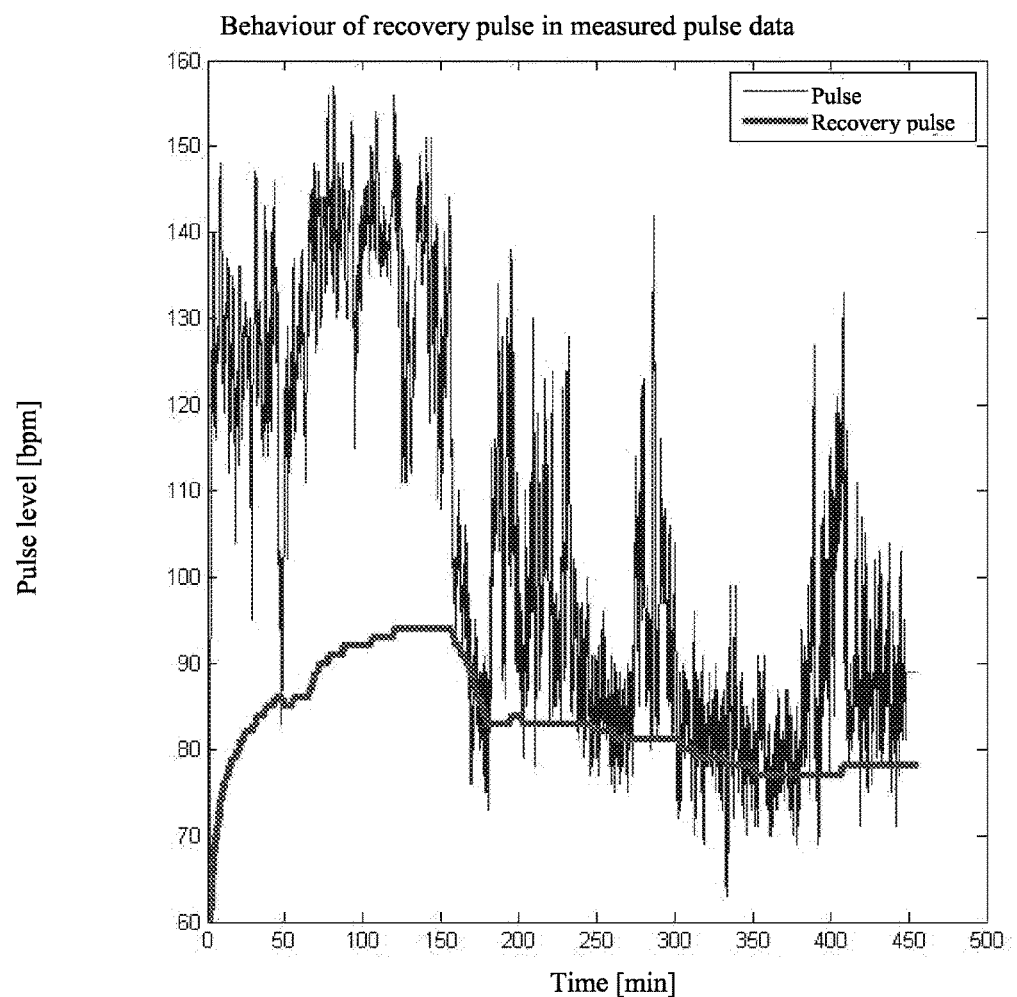
FIG. 8 shows the behavior of recovery pulse during a real exercise.

FIG. 7 shows the saturation levels of recovery pulse relating to one fitness level as a function of pulse level and FIG. 8 shows an example corresponding thereto about the behavior of the recovery pulse during exercise. The described saturation levels are only examples and their actual values can change as the reference material increases and the model is made more accurate. The purpose here, too, is to minimize the mean error between the model and the results of the reference measurements. The values for on response shown in FIG. 7 are listed also in table 1.

TABLE 1

Example of the saturation levels and speeds of recovery pulse as function of intensity in on response. The saturation coefficient corresponds to a situation in which the recovery pulse is updated once every 10 seconds.

| Intensity [% hrr] | Saturation level [% hrr] | Saturation coefficient |
|---|---|---|
| 0 | 0 | 0.00 |
| 10 | 0 | 0.01 |
| 20 | 0 | 0.02 |
| 30 | 2 | 0.03 |
| 40 | 5 | 0.04 |
| 50 | 10 | 0.05 |
| 60 | 13 | 0.06 |
| 70 | 14 | 0.07 |
| 80 | 15 | 0.08 |
| 90 | 23 | 0.09 |
| 100 | 30 | 0.10 |
| 110 | 50 | 0.11 |

Recovery Time Calculation

According to one embodiment the recovery pulse is used for calculating the necessary recovery time.

The calculation of one embodiment is based on the fact that when the pulse is the calculated recovery pulse or lower than that, the recovery time must be reduced; otherwise the recovery time is increased. This is exemplified in FIG. 2 as well, in which a dashed line shows the current pulse and the recovery pulse is shown with a continuous line.

The recovery time depends on the duration of the exercise and its load. In practice the recovery time can be estimated by calculating the effective exercise time connecting all these factors. Thus the measured pulse is put in relation with the maximum performance pulse $HR_{maxperf}$ relating to the duration of the exercise. This relative number is further converted into an effective exercise time addition $\Delta d_{eff}$ by means of a first conversion function f1. For running, the conversion function can be e.g. of the following form:

$$\Delta d_{eff} = f1(HR, HR_{recovery}, HR_{maxperf})$$
$$= (\exp(2 * (HR - HR_{recovery}) / (HR_{maxperf} - HR_{recovery})) - 1) * coeff.$$

In the previous formula $$coeff = coeff(HR, HR_{rest}, HR_{max})$$
$$= 0.00057 * hrr * hrr - 0.11360 * hrr + 7.34503$$

The exact form of the function also depends on the sports. In the above it has been supposed that the measured pulse HR is higher than the calculated recovery pulse. The constant coefficients shown in the formula are examples only.

The function f1 above has been formed using the basic principle that the constant pulse HR is used for reaching the level of maximum performance pulse $HR_{maxperf}=HR$ in a time that corresponds to the world record achieved with the said relative intensity.

The new effective exercise time is the sum of effective exercise time and the addition to the effective exercise time. Thus $$d_{eff\_new} = d_{eff\_old} + \Delta d_{eff}.$$

Figure 3:
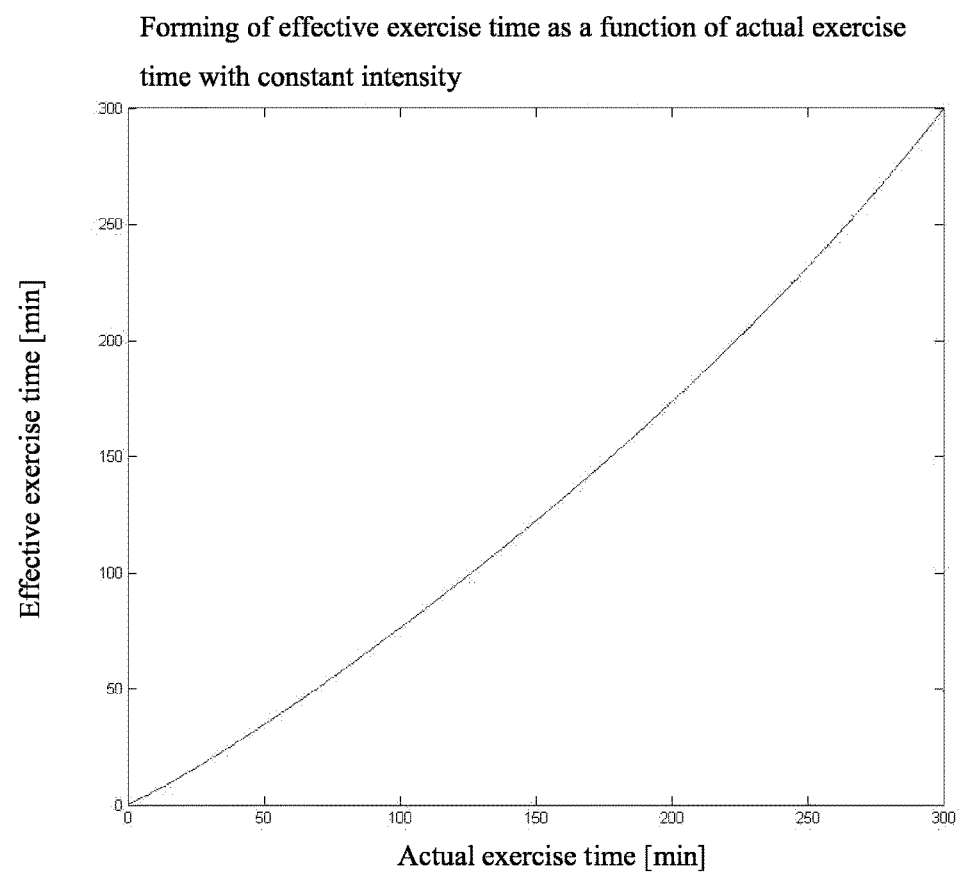
FIG. 3 shows the principal form of the weight coefficient function used in the recovery time calculation.

Thus the weight coefficient function f1 can be a monotonically increasing exponent function in form, determining the accumulation of the effective training time like shown in FIG. 3. With such a function it is possible to take the increase of the load of the performance into account especially with higher pulse levels as a larger increase of recovery time, which corresponds well with the reality.

According to one embodiment, any time the pulse exceeds the maximum performance pulse, the recovery time is increased much, i.e. faster than with the pulse being between the recovery pulse and the maximum performance pulse. Such behavior can be modeled, instead of the exponent function of formula f1, with e.g. a linear piecewise function.

Figure 4:
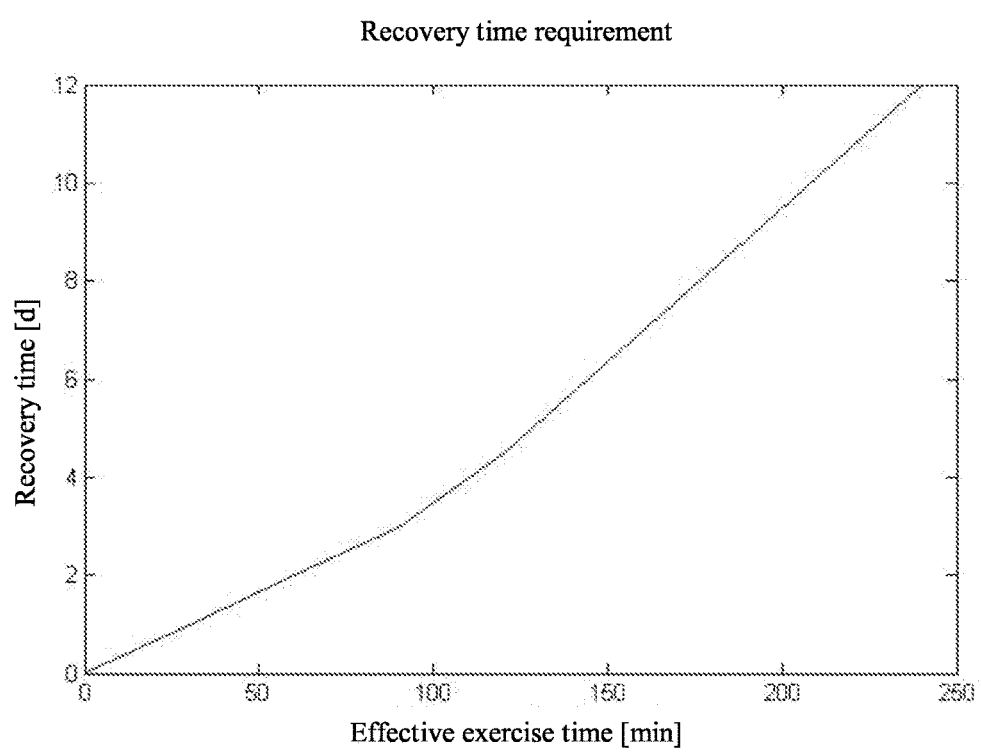
FIG. 4 shows an example of the recovery time in relation to the effective exercise time.

The recovery time can be further produced by converting the effective exercise time to recovery time requirement by means of a second conversion function f2. For example, FIG. 4 contains an example of such conversion function f2. The function f2 can be formed by estimating the recovery requirement from performances of various duration. For example, in running this can be done by tabulating the recovery requirements from maximal performances as a function of distance corresponding to the performance. For example, George Sheehan (1972) suggested that from a performance of 8 km the necessary rest is one week, 16 km two weeks and half marathon a month (freely paraphrased from Lore of Running, Timothy Noakes, 4. edition). These estimates are conservative and they are based on competitive sports. In other words, the recovery requirement calculation is based on empirical observations about recovery from sports performances. Many factors have an effect on recovery, but fitness level has a considerable effect thereon. Thus the function f2 is generally of the form $t_{recovery}=f2(d_{eff},\text{fitness index,sports})$.

Energy Consumption Calculation

According to one embodiment recovery pulse is used for calculating energy consumption.

According to an advantageous embodiment the energy consumption is calculated by using the quantity "percentage of pulse reserve", used also in estimating the recovery pulse, as the basic quantity. However, in the energy calculation formula the recovery pulse $HR_{recovery}$ is used instead of the real resting pulse. This gives the effective pulse level $hrr_{eff}$.

$hrr_{eff}=(HR-HR_{recovery})*100\%/(HR_{max}-HR_{recovery})$.

Figure 5:
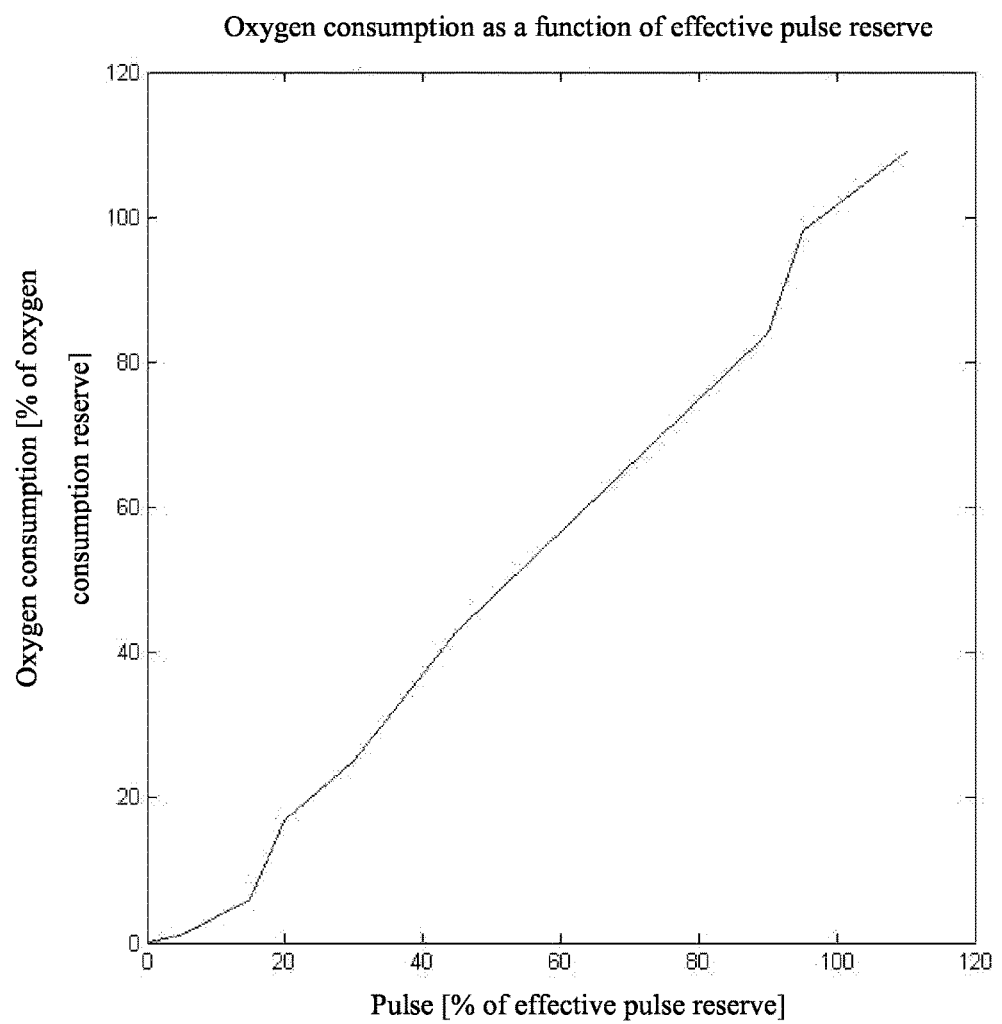
FIG. 5 shows the response of oxygen consumption to rising intensity of the exercise.

For example, the conversion of pulse to a relative oxygen consumption value (VO2 percent of a person's maximal oxygen consumption reserve VO2Max−3.5 ml/kg/min) is shown in FIG. 5. FIG. 5 should not be taken as a physiological "truth" but as a function produced by a modeling minimizing the mean error in relation to reference measurements.

Using the relative oxygen consumption value the oxygen consumption as percentage of the maximal oxygen intake reserve VO2Max−3.5 ml/kg/min (=% $VO2_{reserve}$) can be calculated and this can be converted to energy consumption, if the index describing the fitness of the person, sex, age and weight are known.

VO2Max can be estimated in a way known to one skilled in the art on the basis of material provided by Shvarz and Reibold by arranging suitable functions into the material collected by them. In other words $VO2\text{Max}=f(\text{sex,age,fitness index})$.

When the maximum oxygen intake scale is known, the momentary oxygen consumption value VO2 is produced in units of ml/kg/min.

$VO2=(VO2\text{Max}-3.5 \text{ ml/kg/min})*\% VO2_{reserve}+3.5 \text{ ml/kg/min}$.

The value of 3.5 ml/kg/min in the formula corresponds to oxygen consumption in resting state (calculated average) for which also the unit 1 MET is used.

For energy consumption per minute (unit kcal/min) can be used the following formula, for example (among others ACSM, www.acsm.org)

$\text{Power}=VO2*\text{weight}/200$, where weight is the mass of the person in kilograms and VO2 the oxygen consumption in units ml/kg/min.

Tests have shown that with the above-mentioned model the error in calculation of energy consumption is at most 5 to 10% as compared with the real energy consumption.

It should be noted that the present energy consumption calculation can be made instead of the VO2 quantity with the 1 MET quantity (Metabolic Equivalent of Task) describing the resting state energy consumption and its multiples, as one skilled in the art will understand.

Figure 6:
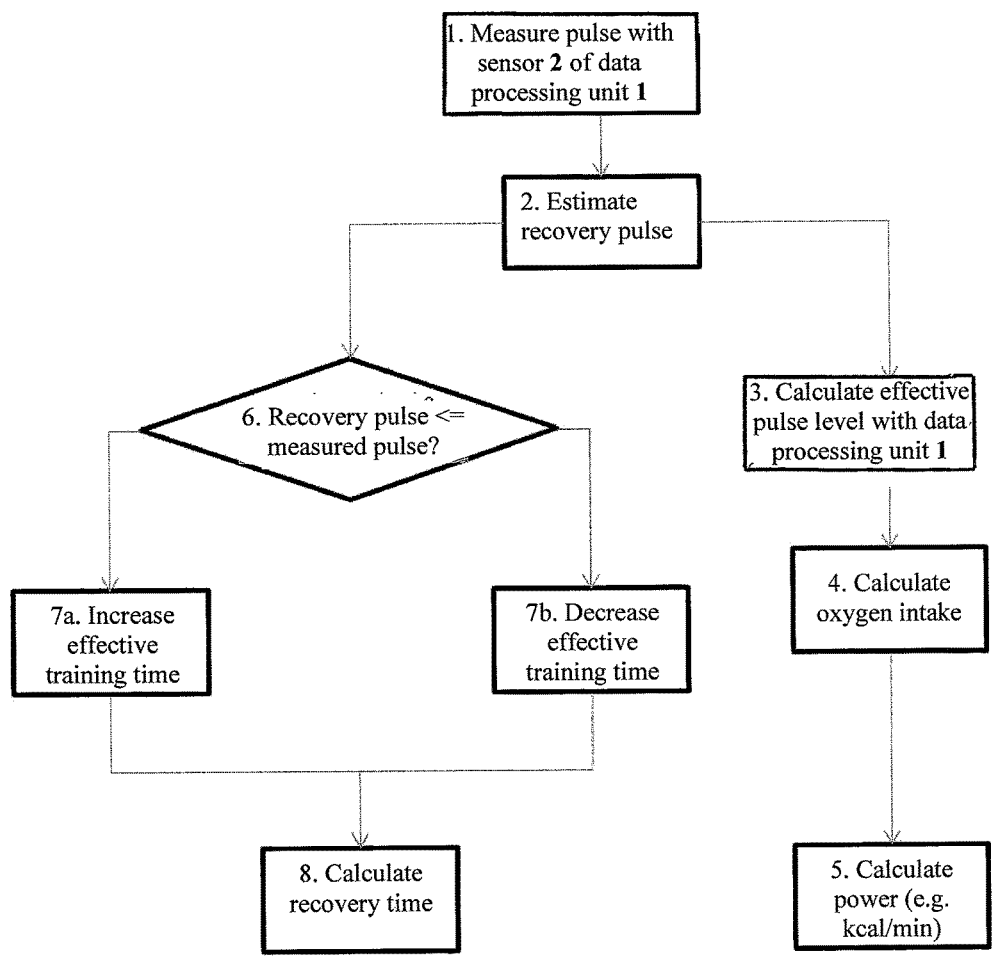
FIG. 6 shows the energy consumption calculation and recovery time calculation according to an embodiment of the invention as a flow diagram.

In the following, reference is made to FIG. 6, in which the above-mentioned methods are shown as flow charts. The method starts at step 1 with measurement of pulse frequency. The measured pulse frequency is put into relation with the resting pulse and the maximum pulse of the person in step 2, which then produces information about the calculated recovery pulse. The calculated recovery pulse is further used in step 3 for estimating the effective pulse level of the person, from which the proportion of oxygen usage of the oxygen usage reserve is calculated in step 4. The calculated oxygen consumption is converted to power produced by the body in step 5 with known formulae.

Figure 9:
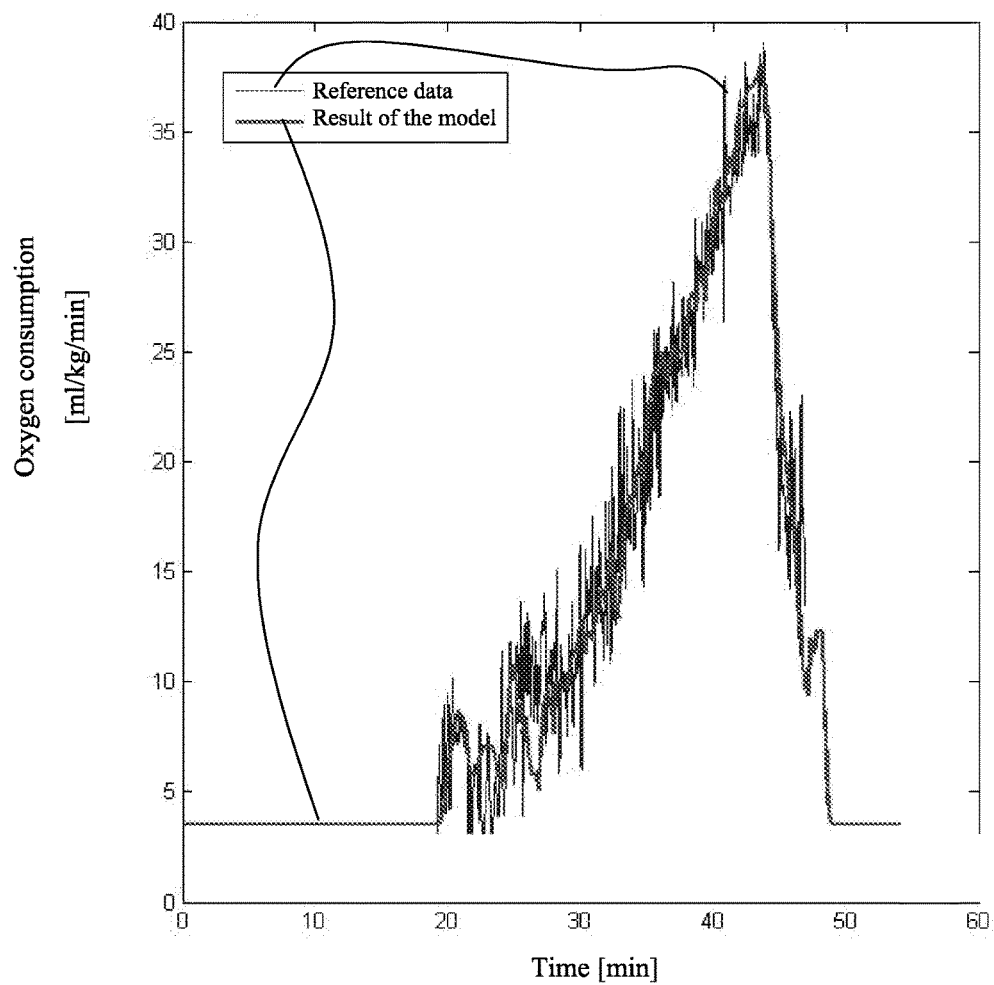
FIG. 9 shows an example of the oxygen consumption calculated by means of the principles described in the invention from which it is further possible to estimate energy consumption.

FIG. 9 shows an example of the result of the calculation compared to the reference measurement.

In step 6 the measured pulse is viewed in relation to the calculated resting pulse. In case the current pulse is higher than the recovery pulse, the effective exercise time is increased (step 7a). If this isn't the case, the effective exercise time is reduced (step 7b). The effective exercise time is converted into recovery time requirement in step 8.

Using the above-mentioned parameters and parameters defined by means of the invention it is possible to calculate also the EPOC (Excess Post-exercise Oxygen Consumption), the training effect or other quantities relating to the intensity of the exercise, as is obvious to one skilled in the art.

Apparatuses suitable for carrying out the present method include wrist computers, laptop computers or desktop computers with means for measuring the pulse or the possibility to input the pulse signal to the apparatus wirelessly or with wires from for example, a pulse belt. In addition to real-time calculation the method can also be used afterwards by using a saved time-related pulse frequency information that can be read from, e.g. a pulse belt capable of storing data.

According to one embodiment the apparatus comprises at least the following components:

Means for measuring the pulse of the heart or for importing the pulse signal from an external pulse sensor. Most typically the apparatus is a wrist computer with means for receiving pulse signal wirelessly from a separate pulse belt.

Data processing unit for determining the pulse value on the basis of pulse or pulse signal and for calculating the said exercise parameter on the basis of the pulse value. The data processing unit can comprise a microprocessor functionally connected to the said means for measuring or receiving the pulse signal.

A memory means for saving the pre-data relating to the physical exercise and/or the person. The memory means can comprise a memory circuit. The pre-data can be factory-installed and/or they can be automatically configured or entered by means of the user interface means of the apparatus.

The data processing unit is arranged to execute the following operations:

Determining the pulse value and the recovery pulse value on the basis of the said pre-data. As has been described in the above, the recovery pulse value describes the pulse level achieved in a certain time after finishing the exercise.

Recursively updating the recovery pulse value during the performance. Due to recursiveness the performance history has an effect on the recovery pulse determined at a given moment corresponding with physiological reality.

Determining the said exercise parameter, such as energy consumption or recovery time, on the basis of the recovery pulse value, for example as has been described above in more detail.

The embodiments and examples described above as well as the appended drawings are meant to illustrate the invention and they do not limit the scope of the invention defined in the appended claims.

We claim:

1. A method for calculating with a computer apparatus having a data processing unit that is functionally connected to a pulse sensor, an exercise parameter after a physical performance by a person, comprising:
measuring a heart rate of the person by the pulse sensor, the data processing unit receiving pulse signals from the pulse sensor that include data about the heart rate,
determining a current pulse value based on the measured heart rate,
determining, during an uninterrupted physical performance, recursively a dynamically variable current recovery pulse value based at least on the current pulse value, predefined pre-data values stored in a memory means, and a previously determined previous recovery pulse value,
said dynamically variable current recovery pulse value indicating a pulse level achieved at a certain time after the performance is interrupted and the person stays still, and
utilizing the data processing unit to compare the determined current pulse value with the predefined pre-data values stored in the memory means to obtain data that characterizes a recovery process of the person, which, based on the current pulse value and the current dynamically variable current recovery pulse value, is used to carry out the computation of said exercise parameter and to provide an output of the same on a user interface of said computer apparatus.

2. A method according to claim 1, further comprising:
deriving the current pulse value from the measured heart rate by a formula using as a factor, a difference between the measured heart rate HR, and a resting heart rate $HR_{rest}$ of the person,
wherein the resting heart rate $HR_{rest}$ of the person is the predefined pre-data stored in memory means.

3. A method according to claim 2, wherein the difference $(HR-HR_{rest})$ is put in relation with an available pulse reserve defined by $(HR_{max}-HR_{rest})$ by using a formula having as a factor $(HR-HR_{rest})(HR_{max}-HR_{rest})$,
where HR is the measured heart rate,
the $HR_{rest}$ is the resting heart rate of the person, and
the $HR_{max}$ is the maximum heart rate of the person.

4. A method according to claim 3, further comprising:
calculating the recovery pulse value using a formula comprising as a factor, an index describing the fitness level of the person.

5. A method according to claim 2, further comprising:
calculating the recovery pulse value using a formula comprising as a factor, an index describing a fitness level of the person.

6. A method according to claim 1, further comprising:
calculating the recovery pulse value by using a formula as a factor, an index describing a fitness level of the person.

7. A method according to claim 1, further comprising:
determining the dynamically variable current recovery pulse value recursively by using a previously determined recovery pulse value, the method comprising:
providing a first table connecting the current pulse values and saturation levels of the recovery pulse values corresponding therewith,
reading from the first table a first saturation level of a specific recovery pulse value corresponding to the current pulse value,
changing the specific recovery pulse value based on the first saturation level.

8. A method according to claim 7, further comprising:
choosing contents of the first table based on whether the current pulse value is larger or smaller than the specific recovery pulse value.

9. A method according to claim 7, further comprising:
providing a second table, the second table connecting the current pulse values and saturation speed coefficients corresponding therewith,
reading from the second table a first saturation speed coefficient corresponding with the current pulse value, and
changing a first recovery pulse value based on the said saturation level and the first saturation speed coefficient.

10. A method according to claim 9, wherein choosing contents of the second table based on an index describing a fitness level of the person.

11. A method according to claim 1, further comprising:
calculating a converted pulse value $((HR-HR_{rest})-HR_{recovery})$ based on the current pulse value by subtracting a recovery pulse value therefrom, and
calculating said exercise parameter by using the converted pulse value.

12. A method according to claim 1, wherein said exercise parameter is a recovery time describing a resting time needed by the person for fully recovering from a current exercise.

13. A method according to claim 12, further comprising:
calculating the recovery time recursively by using a previously determined recovery time so that
each time when the current pulse value is higher than the determined pulse level, the recovery time is increased, and
each time when the current pulse value is lower than or equal to a determined dynamically variable current recovery pulse value, the recovery time is reduced.

14. A method according to claim 12, further comprising:
calculating the recovery time based on an effective exercise time, the effective exercise time being calculated from an actual pulse frequency and a maximum performance pulse, the maximum performance pulse being chosen depending on a type of a sport the person is doing.

15. A method according to claim 12, further comprising:
calculating the recovery time by taking into account an index describing a fitness level of the person.

16. A method according to claim 1, wherein the said exercise parameter is energy consumption.

17. A method according to claim 16, further comprising:
converting the current pulse value into an oxygen consumption value,
calculating the energy consumption based on the oxygen consumption value using an algorithm taking into account sex, age, weight of the person, as well as an index describing a fitness level of the person.

18. A method according to claim 17, further comprising:
converting the current pulse value into the oxygen consumption value using a different conversion depending on whether the current pulse value is lower or higher than the recovery pulse value.

19. A method according to claim 1, wherein:
the determination of the dynamically variable current recovery pulse value comprises the further step of:
providing as a predefined pre-data a first table stored in said memory means, said first table connecting pulse values and saturation levels of recovery pulse values corresponding therewith, reading from the first table a saturation level of a recovery pulse value corresponding to the current pulse value, changing the recovery pulse value on the basis of the said saturation level.

20. A method according to claim 1, wherein the determination of the dynamically variable current recovery pulse value comprises the further steps of:

providing as a predefined pre-data a second table stored in said memory means, said second table connecting the current pulse values and saturation speed coefficients corresponding therewith, reading from the second table a saturation speed coefficient corresponding with the current pulse value, and changing the recovery pulse value on the said saturation level and said saturation speed coefficient.

* * * * *